US008017757B2

(12) United States Patent
Ahn et al.

(10) Patent No.: US 8,017,757 B2
(45) Date of Patent: Sep. 13, 2011

(54) KITS AND METHOD FOR DETECTING HUMAN PAPILLOMA VIRUS WITH OLIGO NUCLEOTIDE BEAD ARRAY

(75) Inventors: Woong Shick Ahn, Seoul (KR); Byoung-Don Han, Seoul (KR); Yong Taek Oh, Seoul (KR); Su Mi Bae, Seoul (KR)

(73) Assignees: Gyngene Bio Co., Ltd, Seoul (KR); Byoung-Don Han, Seoul (KR)

( * ) Notice: Subject to any disclaimer, the term of this patent is extended or adjusted under 35 U.S.C. 154(b) by 382 days.

(21) Appl. No.: 12/095,646

(22) PCT Filed: Feb. 23, 2007

(86) PCT No.: PCT/KR2007/000944
§ 371 (c)(1),
(2), (4) Date: May 30, 2008

(87) PCT Pub. No.: WO2007/100198
PCT Pub. Date: Sep. 7, 2007

(65) Prior Publication Data
US 2008/0311561 A1  Dec. 18, 2008

(30) Foreign Application Priority Data
Mar. 3, 2006 (KR) .......................... 10-2006-0020684

(51) Int. Cl.
*C07H 21/04* (2006.01)
*C12P 19/34* (2006.01)
(52) U.S. Cl. .................................. 536/24.3; 435/91.2
(58) Field of Classification Search .................. None
See application file for complete search history.

(56) References Cited

U.S. PATENT DOCUMENTS

| 5,057,411 A | 10/1991 | Lancaster et al. | |
| 2003/0165821 A1 | 9/2003 | Van Doorn et al. | |
| 2003/0224385 A1* | 12/2003 | Pihan | 435/6 |
| 2005/0175989 A1* | 8/2005 | Lin et al. | 435/5 |
| 2005/0191644 A1* | 9/2005 | Shimamoto et al. | 435/6 |
| 2005/0260561 A1 | 11/2005 | Meijer et al. | |

FOREIGN PATENT DOCUMENTS

| DE | 199903056 A1 | 8/2000 |
| KR | 1020040078506 A | 9/2004 |
| KR | 541916 B1 * | 1/2006 |
| WO | WO 0056898 A1 * | 9/2000 |
| WO | WO 0168915 A1 * | 9/2001 |
| WO | WO 03027323 A1 * | 4/2003 |
| WO | WO 2004050917 A1 * | 6/2004 |
| WO | WO 2005000095 A2 * | 1/2005 |
| WO | WO 2006038753 A1 * | 4/2006 |

OTHER PUBLICATIONS

Oh et al. Polymerase chain reaction-based fluorescent Luminex assay to detect the presence of human papillomavirus types. Cancer Sci 98(4):549-554, published online Feb. 9, 2007.*
GenBank GI:60295 [online] Jan. 7, 1993 [retrieved on Nov. 6, 2010] retrieved from http://www.ncbi.nlm.nih.gov/nuccore/60295?sat=OLDID&satkey=34483.*
GenBank GI:1345087 [online] May 31, 1996 [retrieved on Nov. 6, 2010] retrieved from http://www.ncbi.nlm.nih.gov/nuccore/1345087.*
GenBank GI:1173493 [online] May 30, 1996 [retrieved on Nov. 6, 2010] retrieved from http://www.ncbi.nlm.nih.gov/nuccore/1173493.*
Machine translation of KR 541916 B1, obtained from http://kposd.kipo.go.kr:8088/up/kpion/ on Nov. 5, 2010.*
Godfroid et al, "Detection and identification of human papilloma viral ,DNA, types 16, J8, and 33, by a combination of polymerase chain reaction and a colorimetric solid phase capture hybridisation assay," J Virol Method 1998, 75: 69-81.
Devilliers,"Heterogeneity of the Human Papillomavirus Group," J. Virol 63: 4898-4903, 1989.
Jacobs et al, "Group-Specific Differentiation between High- and Low-Risk Human Papillomavirus Genotypes by General Primer-Mediated PCR and Two Cocktails of Oligonucleotide Probes," J Clin Microbiol, 33: 901-905, 1995.
Menezes et al, "Utility of the in Situ Detection of HPV in Pap Smears Diagnosed as Within Normal Limits," Acta Cytol. 45: 919-926, 2001.
Reid et a, "HPV-Associated Lesions of , the Cervix: Biology and Colposcopic Features," Clin Obstet Gynecol, 1989 32: 157-179.
Lungu et a, "Relationship of Human Papillomavirus Type to Grade of Cervical Intraepithelial Neoplasia," JAMA 267: 2493-2496, 1992.
Qu et al, "PCR Detection of Human Papillomavirus: Comparison between MY09/MY11 and GP51/GP61 Primer Systems," J. Clin Microbiol 35: 1304-1310, 1997.
Karlsen et al, "Use of Multiple peR Primer Sets for Optimal Detection of Human Papillomavirus," J. Cln Microbiol, 1996, 34: 2095-2100.
Gravitt et al, "Improved Amplification of Genital Human Papillomaviruses," J Clin Micribiol 38: 357-361.
Clavel et al, "Hybrid capture II, a new sensitive test for human papillomavirus detection. Comparison with hybrid capture I and PCR results in cervical lesions," J. Clin Pathol 51: 737-740, 1998.
German Translation of Abstract: German Publication No. DE19903056(A1); Applicant: Medeea Forschungs GMBH; Published Aug. 3, 2000 (Abstract Only) (1 PG).
Database Geneseq [Online] Sep. 9, 2004, "Human papillomavirus genotype detection PCR primer #10." XP002535994 (1 PG).
Database EMBL [Online] Jan. 9, 2006, "Sequence 10 from Patent EPI609874." XP002535995 (1 PG).

(Continued)

*Primary Examiner* — Samuel Woolwine
(74) *Attorney, Agent, or Firm* — Casimir Jones SC

(57) ABSTRACT

Provided are determining methods of human papillomavirus (HPV) genotypes with a high sensitivity. The method includes performing two-step PCRs on an HPV L1 gene in a sample to be analyzed as a biotin-labeled, single-stranded L1 gene, performing a hybridization reaction on the biotin-labeled, single-stranded L1 gene with a HPV genotype detection probe, reacting the hybridization reaction product with fluorescent substance combined with streptavidine, and measuring a fluorescent substance level to identify the HPV genotype. The detection method has high sensitivity enough to detect an extremely small amount of HPV in the sample. In addition, the high specificity exhibited by the detection method enables accurate diagnosis specific to HPV type.

12 Claims, 2 Drawing Sheets

OTHER PUBLICATIONS

Database Geneseq [Online] Apr. 10, 1996, "Human papilloma virus 16 specific oligonucleotide probe MY97." XP002535996 (1 PG).

Hormia Marketta et al: "Marginal periodontium as a potential reservoir of human papillomavirus in oral mucosa" Journal of Periodontology, vol. 76, No. 3, Mar. 2005, pp. 358-363.

Fischer Markus: "Investigation of a 1,2,5-19 broad-spectrum PCR assay for human papillomaviruses in screening benign lesions of the upper aerodigestive tract" ORL (BASEL), vol. 67, No. 4, 2005, pp. 237-241.

Nelson Joshua H et al: "A novel and rapid 1,2,5-19 PCR-based method for genotyping human papillomaviruses in clinical samples" Journal of Clinical Microbiology, vol. 38, No. 2, Feb. 2000, pp. 688-695.

Husnjak Koraljka et al: "Comparison of 1,2,5-19 five different polymerase chain reaction methods for detection of human papillomavirus in cervical cell specimens" Journal of Virological Methods, vol. 88, No. 2, Aug. 2000, pp. 125-134.

English Translation of Abstract: Korean Publication No. KR1020040078506 A; Applicant: Biomaedrab Co., Ltd; Published Sep. 10, 2004 (1 PG) Abstract Only.

English Translation of Abstract: German Publication No. DE199903056 A1; Applicant: Medeea Forschungs GMBH; Published Aug. 3, 2000 (1 PG) Abstract Only.

\* cited by examiner

SEQUENCE LISTING

<160> NUMBER OF SEQ ID NOS: 30

<210> SEQ ID NO 1
<211> LENGTH: 23
<212> TYPE: DNA
<213> ORGANISM: Artificial Sequence
<220> FEATURE:
<223> OTHER INFORMATION: Synthetic

<400> SEQUENCE: 1
tgtgctgcca tatctacttc aga                                          23

<210> SEQ ID NO 2
<211> LENGTH: 20

```
<212> TYPE: DNA
<213> ORGANISM: Artificial Sequence
<220> FEATURE:
<223> OTHER INFORMATION: Synthetic

<400> SEQUENCE: 2
agtctcctgt acctgggcaa                                               20

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
gtgctgcaat tgcaaacagt                                               20

<210> SEQ ID NO 4
<211> LENGTH: 27
<212> TYPE: DNA
<213> ORGANISM: Artificial Sequence
<220> FEATURE:
<223> OTHER INFORMATION: Synthetic

<400> SEQUENCE: 4
tgcacacaag taactagtga cagtaca                                       27

<210> SEQ ID NO 5
<211> LENGTH: 23
<212> TYPE: DNA
<213> ORGANISM: Artificial Sequence
<220> FEATURE:
<223> OTHER INFORMATION: Synthetic

<400> SEQUENCE: 5
ctgtgtgttc tgctgtgtct tct                                           23

<210> SEQ ID NO 6
<211> LENGTH: 27
<212> TYPE: DNA
<213> ORGANISM: Artificial Sequence
<220> FEATURE:
<223> OTHER INFORMATION: Synthetic

<400> SEQUENCE: 6
ttccatacct tctacatatg atccttc                                       27

<210> SEQ ID NO 7
<211> LENGTH: 22
<212> TYPE: DNA
<213> ORGANISM: Artificial Sequence
<220> FEATURE:
<223> OTHER INFORMATION: Synthetic

<400> SEQUENCE: 7
gctgaggtta aaaggaaag ca                                             22

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
cacaaaatcc tgtgccaagt                                               20
```

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
attagcactg ccactgctgc                                                    20

<210> SEQ ID NO 10
<211> LENGTH: 27
<212> TYPE: DNA
<213> ORGANISM: Artificial Sequence
<220> FEATURE:
<223> OTHER INFORMATION: Synthetic

<400> SEQUENCE: 10
ttctgtgtgt gcttctacta cttcttc                                            27

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
ccgcaaccac acagtctatg                                                    20

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
catccacgca ggatagcttt                                                    20

<210> SEQ ID NO 13
<211> LENGTH: 27
<212> TYPE: DNA
<213> ORGANISM: Artificial Sequence
<220> FEATURE:
<223> OTHER INFORMATION: Synthetic

<400> SEQUENCE: 13
cagttaagta aatatgatgc acgaaaa                                            27

<210> SEQ ID NO 14
<211> LENGTH: 23
<212> TYPE: DNA
<213> ORGANISM: Artificial Sequence
<220> FEATURE:
<223> OTHER INFORMATION: Synthetic

<400> SEQUENCE: 14
tgcactgaag taactaagga agg                                                23

<210> SEQ ID NO 15
<211> LENGTH: 23
<212> TYPE: DNA
<213> ORGANISM: Artificial Sequence
<220> FEATURE:
<223> OTHER INFORMATION: Synthetic

<400> SEQUENCE: 15
aactaaatat gatgcccgtg aaa                                              23

<210> SEQ ID NO 16
<211> LENGTH: 26
<212> TYPE: DNA
<213> ORGANISM: Artificial Sequence
<220> FEATURE:
<223> OTHER INFORMATION: Synthetic

<400> SEQUENCE: 16
tcagctgtac caaatattta tgatcc                                           26

<210> SEQ ID NO 17
<211> LENGTH: 22
<212> TYPE: DNA
<213> ORGANISM: Artificial Sequence
<220> FEATURE:
<223> OTHER INFORMATION: Synthetic

<400> SEQUENCE: 17
gcatccgtaa ctacatcttc ca                                               22

<210> SEQ ID NO 18
<211> LENGTH: 23
<212> TYPE: DNA
<213> ORGANISM: Artificial Sequence
<220> FEATURE:
<223> OTHER INFORMATION: Synthetic

<400> SEQUENCE: 18
tgtgcatctg tgtctaaatc tgc                                              23

<210> SEQ ID NO 19
<211> LENGTH: 21
<212> TYPE: DNA
<213> ORGANISM: Artificial Sequence
<220> FEATURE:
<223> OTHER INFORMATION: Synthetic

<400> SEQUENCE: 19
tccacaagta caactgcacc a                                                21

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
cccacaccaa ccccatataa                                                  20

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
ccactgcaac atctggtgat                                                  20

<210> SEQ ID NO 22
<211> LENGTH: 20

```
<212> TYPE: DNA
<213> ORGANISM: Artificial Sequence
<220> FEATURE:
<223> OTHER INFORMATION: Synthetic

<400> SEQUENCE: 22
ctgaccctac tgtgcccagt                                                    20

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
cactacacag tccccctccgt                                                   20

<210> SEQ ID NO 24
<211> LENGTH: 19
<212> TYPE: DNA
<213> ORGANISM: Artificial Sequence
<220> FEATURE:
<223> OTHER INFORMATION: Synthetic

<400> SEQUENCE: 24
tgcaccgaaa cggccatac                                                     19

<210> SEQ ID NO 25
<211> LENGTH: 32
<212> TYPE: DNA
<213> ORGANISM: Artificial Sequence
<220> FEATURE:
<223> OTHER INFORMATION: Synthetic

<400> SEQUENCE: 25
tttgttactg ttgtagatac tacccgtagc ac                                      32

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
aatcccatca ccatcttcca                                                    20

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
gcmcagggwc ayaayaatgg                                                    20

<210> SEQ ID NO 28
<211> LENGTH: 24
<212> TYPE: DNA
<213> ORGANISM: Artificial Sequence
<220> FEATURE:
<223> OTHER INFORMATION: Synthetic

<400> SEQUENCE: 28
aataaactgt aaatcatatt cctc                                               24
```

```
<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
gagtcaacgg atttggtcgt                                              20

<210> SEQ ID NO 30
<211> LENGTH: 20
<212> TYPE: DNA
<213> ORGANISM: Artificial Sequence
<220> FEATURE:
<223> OTHER INFORMATION: Synthetic

<400> SEQUENCE: 30
ttgattttgg agggatctcg                                              20
```

KITS AND METHOD FOR DETECTING HUMAN PAPILLOMA VIRUS WITH OLIGO NUCLEOTIDE BEAD ARRAY

TECHNICAL FIELD

The present invention relates to a kit and method for genotyping human papillomavirus (HPV) with a high sensitivity and specificity.

BACKGROUND ART

Human papillomaviruses (HPV) are known to be approximately 8 kb DNA viruses and to be closely associated with various malignant tumors, causing uterine cervical cancer to women (Godfroid et al., J. Virol. Method 75:69-81, 1998).

The uterine cervical cancer has been considered to be closely associated with sexual contact, and an HPV infection, which is one of the most common sexually transmitted diseases, is involved in incidences of uterine cervical carcinogenesis. To date, approximately 100 HPV genotypes have been identified; approximately 30 types have been proved to be closely related to cervical cancer, which are subdivided into a "high-risk" HPV type group (e.g. 16, 18, 31, 33, or 35 type) and a "low-risk" HPV type group (e.g. 6, 11, 42, 43, or 44 type) (De Villiers, J. Virol. 63:4898-4903, 1989; Jacobs et al., J. Clin. Microbiol. 33:901-905, 1995.).

The cervical cancer is currently diagnosed by a combination of several diagnostic tests. Among these, the most commonly used for diagnosis of cervical cancer is a Papanicolaou (Pap) smear test. However, the Pap smear test primarily relies on expert's ability, false or inaccurate test results are frequently appeared (Menezes et al., Acta Cytol. 45:919-926, 2001). Colposcopic screening enables HPV infections to be detected relatively accurately, that is, up to 70% of detection rate. However, the colposcopic screening is also problematic because it is incapable of determining HPV genotypes to classify high- and low-risk genotypes. On the other hand, it is a costly procedure and requires a highly-trained expert and expensive equipment (Reid et al., Clin Obstet. Gynecol. 32:157-179, 1989).

A PCR-RFLP method, which uses restriction enzymes after PCR (polymerase chain reaction) amplification of HPV a region of L1 region is accomplished, enables detection results to be obtainable easily and simply. However, according to this method, if variants are not identified by the restriction enzymes used, a highly sensitive assay is not available (Lungu et al., JAMA 267:2493-2496, 1992). In addition, the efficiency of PCR amplification may vary according to HPV genotypes, which may undesirably reduce accuracy of the assay (Qu et al., J. Clin. Microbiol. 35:1304-1310, 1997; Karksen et al., J. Clin. Microbiol. 34:2095-2100, 1996; Gravitt et al., J. Clin. Microbiol. 38:357-361). Further, commercially available hybrid capture kit (Digene, Inc., USA) is identifiable without PCR amplification and they can classify high-risk and low-risk HPV groups. However, the hybrid capture kit cannot distinguish between HPV genotypes 16 and 18, which are highly related with the uterine cervical cancer, and other high-risk HPV genotypes (Clavel et al., J. Clin. Pathol. 51:737-740, 1998). HPV genotype assay kits (BioMedLab., Co., Korea) using HPV DNA chips, which have recently been developed, are subjected to 2-dimensional hybridization on slides, followed by three washing steps, which is quite a burdensome work.

Similarly, HPV detection kits using suspension arrays are currently available. However, the HPV kit exhibits very low signal values for detection, suggesting that there may be limitations in actual detection of low concentrations of infecting viruses, particularly when two or more viruses are co-infected. In addition, to confirm whether there are any other genotypes of HPV without probe on chip or bead or to check a PCR reaction has been carried out properly, the detection technique using micro-array kits requires a number of additional post-PCR steps, such as electrophoresis of PCR products, which are quite burdensome and manageable tasks.

Accordingly, it would be highly desirable to develop high-sensitivity, HPV type detection methods which can accurately detect with extremely low concentrations of HPV types contained in a reagent.

Under these circumstances, the present inventors have tried to detect HPV types with a high sensitivity through the improvement of detection methods especially in the probes for HPV genotype. The present inventors produced detection probes having nucleic acid sequences capable of specifically detecting HPV types from a region of L1 gene with highly heterogeneity between different HPV types. Then, the region was subjected to primary PCR amplification, followed by labeling with a HPV type detection probe to yield a biotin-labeled, single-stranded target molecules. With this labeling methods, the present inventors confirmed that the signal intensity of current labeling methods is approximately 10 times higher than that produced by the conventional method. Further, as described above, the present inventor developed a hybridization probe reacting with all HPV genotypes, enabling even rare HPV infections to be detected without electrophoresis, unlike in the conventional detection probe. In addition, in order to determine whether a PCR reaction has been carried out successfully, GAPDH gene existing in the sample all the time was also amplified and reacted with the hybridization probe for positive control.

DISCLOSURE OF THE INVENTION

The present invention provides a probe for detecting one or more human papillomavirus (HPV) genotypes selected from nucleic acid sequences of SEQ ID NOs: 1-24.

The present invention also provides a probe for detecting a human papillomavirus (HPV) genotype having nucleic acid sequence of SEQ ID NO: 25 reacting with any rare HPV genotypes.

The present invention further provides a set of primers for amplifying a region of human papillomavirus (HPV) L1 gene having nucleic acid sequences of SEQ ID NOs: 27 and 28.

The present invention still further provides a set of primers for amplifying a GAPDH (glyceraldehyde-phosphate dehydrogenase) gene, the primers having nucleic acid sequences of SEQ ID NOs: 29 and 30.

The present invention also provides a GAPDH gene probe base sequence having an nucleic acid sequence of SEQ ID NO: 26 hybridizing specifically to a GAPDH gene amplified with primers having nucleic acid sequences of SEQ ID NOs: 29 and 30.

The present invention also provides a probe for detecting human papillomavirus (HPV) genotypes comprising the probe and/or the primer set.

The present invention also provides a method for determining human papillomavirus (HPV) genotypes with high sensitivity, the method comprising:

(1) performing primary PCR amplification on a region of HPV L1 gene in a sample using a set of forward and reverse primers specific to target sequence; (2) performing secondary PCR amplification on the primary PCR amplicons using a forward or reverse primer to yield a biotin-labeled, single-stranded a region of L1 gene; (3) hybridizing the single-stranded, biotin-labeled secondary PCR amplification product with the HPV genotype detection probe; (4) labeling the hybridization reaction product with fluorescent substance combined with streptavidin; and (5) measuring a fluorescent substance level to identify the HPV genotype.

BEST MODE FOR CARRYING OUT THE INVENTION

Figure 1:
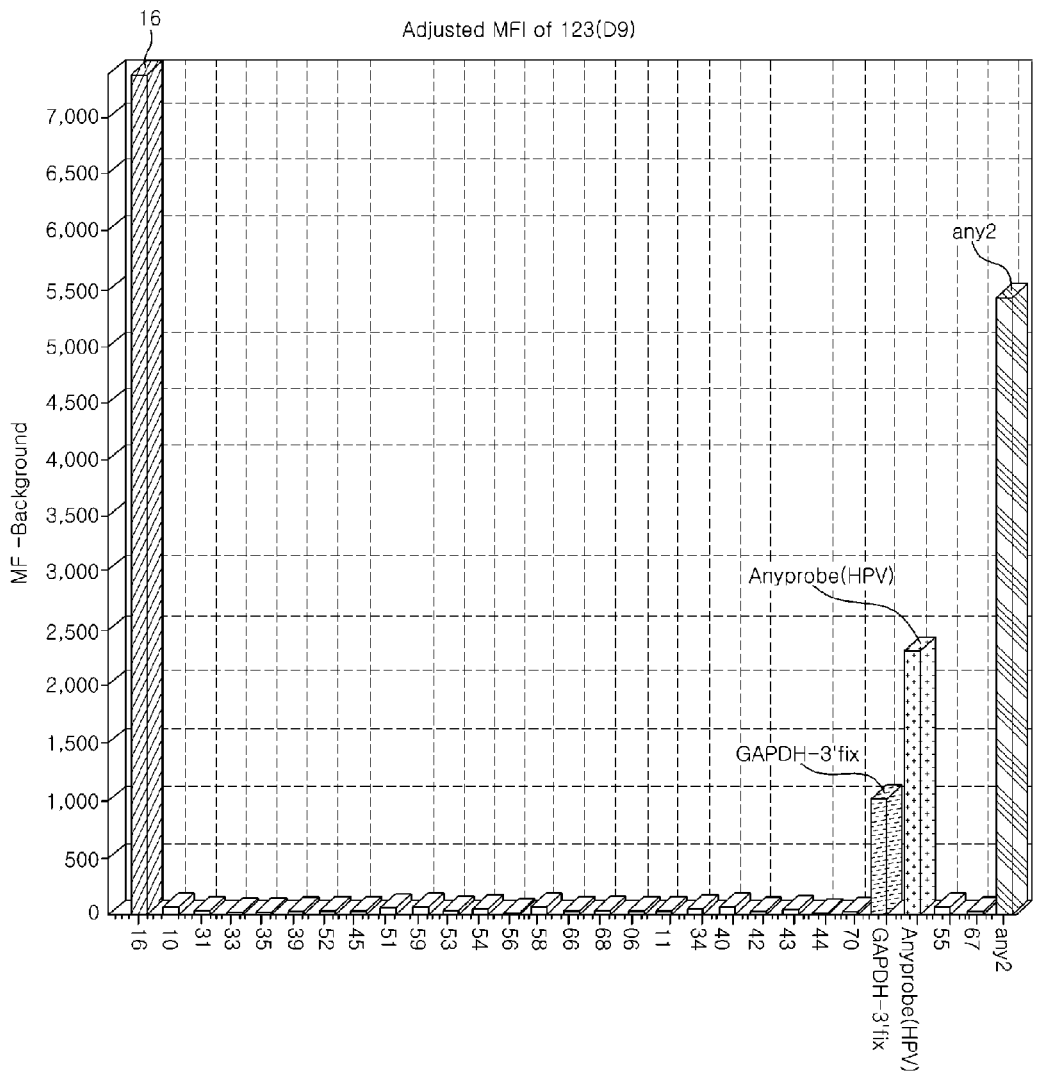
FIG. 1 is showing the analysis result of patient sample using a bead array. As confirmed from FIG. 1, the sample is infected with an HPV type 16 and a signal of a GAPDH gene for positive control and a signal of any probe having nucleic acid sequence of SEQ ID NO: 25 reacting with any HPV types for assay rare HPV types whose probes are not provided in the bead array.

In an aspect, the invention relates to a probe for detecting a human papillomavirus (HPV) genotype.

In one specific aspect, the invention relates to a probe for detecting one or more human papillomavirus (HPV) genotypes selected from nucleic acid sequences of SEQ ID NOs: 1-24.

In another specific aspect, the invention relates to a probe for detecting one or more human papillomavirus (HPV) genotypes having a nucleic acid sequence of SEQ ID NO: 25 reacting with any rare HPV genotypes.

The term "probe" according to the present invention refers to relatively short nucleic acid sequences capable of specifically determining HPV types. Preferably the probe is a nucleic acid molecule of about several to several tens of bases in length. In Table 1, sequences of L1 genotype specific probes are demonstrated for various HPV types provided in the present invention, the probes having nucleic acid sequences of SEQ ID NOs: 1-24. The probes having nucleic acid sequences of SEQ ID NOs: 1-24 exhibit little cross reactivity with other HPV types produced in consideration of the resion of HPV L1 gene specific sequence for each type. When the sample is hybridized using the probes having nucleic acid sequences of SEQ ID NOs: 1-24, the probes enable accurate detection and diagnosis specifically to HPV subtype due to their high specificity and sensitivity. In addition, the probe having a nucleic acid sequence of SEQ ID NO: 25, provided, in the present inventions has a specific sequence reacting with any HPV genotypes, irrespective of HPV type. When the sample is hybridized using the probe having a nucleic acid sequence of SEQ ID NO: 25, hybridizations are carried out with both HPV types capable of hybridizing with the probes having nucleic acid sequences of SEQ ID NOs: 1-24 and HPV types incapable of hybridizing therewith, thereby specifically detecting and diagnosing rare HPV types. Furthermore, in order to simply determine an HPV infection, the present invention provides a method of detecting a probe having a nucleic acid sequence of SEQ ID NO: 25 uses a bead array analyzer, instead of a conventional analyzing method in which a PCR product is subjected to electrophoresis prior to HPV subtyping. According to the present invention, rare HPV types (which are not included in specific probes) can be determined by detecting the probe having a nucleic acid sequence of SEQ ID NO: 25 without performing electrophoresis. In addition, even if an HPV infection is not detected by electrophoresis due to its low concentration, the HPV infection can be identified, suggesting that convenience and accuracy in detection and diagnosis are improved.

The respective probes provided in the present invention are modified in the following manners. One exemplary probe of the present invention may comprise 5 to 20 thymine (dTTP) sequences on the 5' end. In addition, the probe may comprise a 5' terminal amine group covalently binding with a carboxyl group of the bead. The amine group is preferably linked through a $(CH_2)n$ chain. Here, n is a number in a range between 5 and 10, preferably between 5 and 7. In a specific example of the present invention, each probe is designed to have 15 thymine (dTTP) groups, a $(CH_2)_6$ chain and an amine group. Numerous variations of the nucleic acid sequences of the probe can be made by those of ordinary skill in the art.

Another aspect of the present invention is to provide an amplification primer set of human papillomavirus (HPV) genotypes having nucleic acid sequences of SEQ ID NOs: 27 and 28.

The expression "primer set" of the present invention refers to short nucleic acid sequences capable of producing a pair of bases with complementary templates and capable of acting as a point of initiation for synthesis of template strand to be copied. The primer set provided in the present invention comprises forward and reverse primers designed to amplify all types of a specific region of HPV L1 genes, irrespective of HPV type. In a specific example of the present invention, the primer set has nucleic acid sequences of SEQ ID NOs: 27 and 28.

Another aspect of the present invention provides a primer set for amplifying a GAPDH gene having nucleic acid sequences of SEQ ID NOs: 29 and 30 to confirm whether a PCR reaction has been carried out successfully or not.

The GAPDH primer set provided in the present invention is designed to specifically amplify a GAPDH gene expressed all the time as an intrinsic gene in the sample. In a specific example of the present invention, the GAPDH primer set is a primer set having nucleic acid sequences of SEQ ID NOs: 29 and 30.

Still another aspect of the present invention provides a probe having a nucleic acid sequence of SEQ ID NO: 26 specific probe sequence for a GAPDH gene for detecting an amplified GAPDH gene. This probe is hybridized simultaneously with other HPV specific probes during hybridization to the amplicons of sample. That is, since successful performance of the PCR reaction is immediately determined by the bead array analyzer, the number of undetectable cases due to failures of PCR amplifications can be considerably reduced.

A further aspect of the present invention provides a detection kit of a human papillomavirus (HPV) genotype comprising the probe kit.

The probe kit may be provided in various types according to purposes. Preferably, the kit for the probe is a bead array that combined HPV genotyping probe with a bead.

Apart from the HPV type detecting probe, the detection kit according to the present invention may further comprise a primer sequence for amplifying a region of HPV L1 gene. In addition, the detection kit according to the present invention may further comprise a primer sequence for amplifying a GAPDH gene. Furthermore, the detection kit according to the present invention may further comprise a probe having a sequence specific to the GAPDH gene.

Apart from the above, the detection kit according to the present invention may further comprise the following components: an amplification tube or another suitable container; a reaction buffered solution; deoxyribonucleotides (dNTPs); biotinylated dNTPs; a DNA polymerase; sterile water; and so on. Further, the detection kit according to the present invention may comprise positive and negative control groups.

Another aspect of the present invention is to provide a method for determining human papillomavirus (HPV) genotypes with a high sensitivity, the method comprising: (1) performing primary PCR amplification on a region of HPV L1 gene in a sample using a set of forward and reverse primers specific to target sequence; (2) performing secondary PCR amplification on the primary PCR amplicons using a forward or reverse primer to yield a biotin-labeled, single-stranded a region of L1 gene; (3) hybridizing the single-stranded, biotin-labeled secondary PCR amplification product with the HPV genotype detection probe; (4) labeling the hybridization reaction product with fluorescent substance combined with streptavidin; and (5) measuring a fluorescent substance level to identify the HPV genotype.

Specifically, the present invention provides a method for determining human papillomavirus (HPV) genotypes with a high sensitivity, the method comprising: (1) performing primary PCR amplification on a region of HPV L1 gene and GAPDH gene in a sample using a set of forward and reverse primers specific to the region of L1 gene and the GAPDH gene; (2) performing secondary PCR amplification on the primary PCR amplification products of the L1 gene and the GAPDH gene using a forward or reverse primer, to yield a biotin-labeled, single-stranded L1 gene; (3) simultaneously performing hybridization reactions on both the secondary PCR amplification products of the biotin-labeled, single-stranded L1 and GAPDH genes with a HPV genotype detection probe and a GAPDH specific probe, respectively; (4) labeling the hybridization reaction products with fluorescent substance combined with streptavidin; and (5) measuring fluorescent substance levels to identify the HPV genotype.

The present invention is characteristic in that the PCRs of the step (1) and (2) are sequentially carried out. Through the sequential PCRs, the HPV L1 gene in a sample to be analyzed is amplified and prepared as a biotin-labeled single-stranded L1 gene, enabling high-sensitivity detection. In addition, the GAPDH gene is also amplified and prepared as a biotin-labeled single-stranded gene. In step (1), PCR amplification is performed on the HPV L1 gene using a set of forward and reverse primers specific to the L1 gene derived from a sample DNA. In this step, the L1 gene is exponentially amplified. In a specific example of the present invention, to achieve single-strand amplification, a primer set having nucleic acid sequences of SEQ ID NOs: 27 and 28 is used. Based on the same principle as above, in a specific example of the present invention, the GAPDH gene was amplified and prepared as an amplified GAPDH gene having nucleic acid sequences of SEQ ID NOs: 29 and 30.

In step (2), PCR liner amplification is performed on the HPV L1 gene and/or GAPDH gene amplified in step (I) using biotin-labeled nucleotides. In this step, the L1 gene is (labeled with biotin-nucleotides) linearly amplified. In a specific example of the present invention, to achieve single-strand amplification, a forward or reverse primer is used. When a hybridized probe is an anti-sense strand, a sense strand is amplified using a forward primer. On the other hand, when a hybridized probe is a sense strand, an anti-sense strand is amplified using a reverse primer. Biobin-labeling of the L1 gene and the GAPDH gene may be performed using a biotin-labeled primer or by performing PCR in the presence of biotin-labeled dNTP. In a specific example of the present invention, PCR is performed using a reverse primer having an nucleic acid sequence of SEQ ID NO: 28 and a reverse primer having an nucleic acid sequence of SEQ ID NO: 30 in the presence of biotin-labeled dCTP, thereby preparing biotin-labeled single-stranded genes.

In other words, the exponentially amplified genes produced from the PCR in step (1) and only the strand complementary to the probe is (labeled) amplified by the PCR in step (2), thereby increasing the efficiency of hybridization between the probe and the biotin-labeled gene products. During the PCR in step (1) or (2), the time, temperature and cycles of denaturation, coupling, and combination may be appropriately adjusted.

In step (3), the biotin-labeled single-stranded genes products prepared in step (1) and (2) are hybridized with the probe for determining the HPV type according to the present invention. Here, HPV specific probes having nucleic acid sequences of SEQ ID NOs: 1-24, a probe having a nucleic acid sequence of SEQ ID NO: 30 only for confirmation of HPV presence or absence, and a GAPDH specific probe having a nucleic acid sequence of SEQ ID NO: 29, are preferably used as the detection probes in step (3).

The probe of the present invention may be provided as a bead array. The type of the bead combined with the probe is not particularly limited and the bead array may be produced by the common method well known in the art.

During the hybridization reaction, the kind of buffer used, time and temperature may be appropriately adjusted. In a specific example of the present invention, the hybridization reaction is performed for 5 minutes at 95° C. using a 2× Hybrisol buffer (YeBT., Co. LTD.), followed by further reacting the primarily hybridized product for 3 minutes at 40° C. At this stage, rinsing step is performed using a TM hybridization buffer (0.2 M NaCl, 0.1M Tris(pH 8.0), 0.08% Triton X-100).

In steps (4) and (5), the reactivity between the probe and the sample prepared in the above-described manner is identified based on fluorescence using fluorescent substance combined with streptavidin. Since straptavidine is specifically combined with biotin, a target gene present in a sample can be measured by fluorescence.

Examples of the fluorescent substance include, but not limited to, fluorescein, isothiocyanate, rhodamine, phycoerythrin, picocyanin, allophycocyanin, o-phthaldehyde, and fluorescarmine. In the present invention, phycoerythrine is used by way of example.

In a case where the HPV gene derived from the sample of the present invention is prepared as a biotin-labeled single-stranded a region of L1 gene, the signal value is about 10 times higher than that in the conventional case where the double-stranded PCR product is directly marked by fluorescence. Accordingly, the present invention provides a method for detecting HPV genotypes with a high sensitivity, by which even a trivial amount of HPV genotypes can be diagnosed accurately and simply at an early stage before amplification of the HPV genotypes.

Alterations and additional applications of the invention as illustrated herein, are to be considered within the scope of the invention. The invention is further described with reference to the following examples and it will nevertheless be understood that no limitation of the scope of the invention is thereby intended.

EXAMPLE 1

Preparation of Probes and Bead Array

1-1. Preparation of Probes 20- to 27-mer oligonucleotide probes comprising 15 thymines (dTTP), 6 (CH$_2$) chains and amine group, inclusive of HPV L1 gene, on the 5', are immobilized to a bead array included in the detection kit.

Table 1 shows various probes used to detect HPV genotypes.

TABLE 1

| | | |
|---|---|---|
| Probe 1 type 16 | 5'-TGTGCTGCCATATCTACTTCAGA-3'<br>(SEQ ID NO: 1) | |
| Probe 2 type 18 | 5'-AGTCTCCTGTACCTGGGCAA-3'<br>(SEQ ID NO: 2) | |
| Probe 3 type 31 | 5'-GTGCTGCAATTGCAAACAGT-3'<br>(SEQ ID NO: 3) | |
| Probe 4 type 33 | 5'-TGCACACAAGTAACTAGTGACAGTACA-3'<br>(SEQ ID NO: 4) | |
| Probe 5 type 35 | 5'-CTGTGTGTTCTGCTGTGTCTTCT-3'<br>(SEQ ID NO: 5) | |
| Probe 6 type 39 | 5'-TTCCATACCTTCTACATATGATCCTTC-3'<br>(SEQ ID NO: 6) | |
| Probe 7 type 52 | 5'-GCTGAGGTTAAAAAGGAAAGCA-3'<br>(SEQ ID NO: 7) | |
| Probe 8 type 45 | 5'-CACAAAATCCTGTGCCAAGT-3'<br>(SEQ ID NO: 8) | |
| Probe 9 type 51 | 5'-ATTAGCACTGCCACTGCTGC-3'<br>(SEQ ID NO: 9) | |
| Probe 10 type 59 | 5'-TTCTGTGTGTGCTTCTACTACTTCTTC-3'<br>(SEQ ID NO: 10) | |
| Probe 11 type 53 | 5'-CCGCAACCACACAGTCTATG-3'<br>(SEQ ID NO: 11) | |
| Probe 12 type 54 | 5'-CATCCACGCAGGATAGCTTT-3'<br>(SEQ ID NO: 12) | |
| Probe 13 type 56 | 5'-CAGTTAAGTAAATATGATGCACGAAAA-3'<br>(SEQ ID NO: 13) | |
| Probe 14 type 58 | 5'-TGCACTGAAGTAACTAAGGAAGG-3'<br>(SEQ ID NO: 14) | |
| Probe 15 type 66 | 5'-AACTAAATATGATGCCCGTGAAA3'<br>(SEQ ID NO: 15) | |
| Probe 16 type 68 | 5'-TCAGCTGTACCAAATATTTATGATCC-3'<br>(SEQ ID NO: 16) | |
| Probe 17 type 06 | 5'-GCATCCGTAACTACATCTTCCA-3'<br>(SEQ ID NO: 17) | |
| Probe 18 type 11 | 5'-TGTGCATCTGTGTCTAAATCTGC-3'<br>(SEQ ID NO: 18) | |
| Probe 19 type 34 | 5'-TCCACAAGTACAACTGCACCA-3'<br>(SEQ ID NO: 19) | |
| Probe 20 type 40 | 5'-CCCACACCAACCCCATATAA-3'<br>(SEQ ID NO: 20) | |
| Probe 21 type 42 | 5'-CCACTGCAACATCTGGTGAT-3'<br>(SEQ ID NO: 21) | |
| Probe 22 type 43 | 5'-CTGACCCTACTGTGCCCAGT3'<br>(SEQ ID NO: 22) | |

TABLE 1-continued

| | | |
|---|---|---|
| Probe 23 type 44 | 5'-CACTACACAGTCCCCTCCGT3'<br>(SEQ ID NO: 23) | |
| Probe 24 type 70 | 5'-TGCACCGAAACGGCCATAC-3'<br>(SEQ ID NO: 24) | |
| Probe 25 Any | 5'-TTTGTTACTGTTGTAGATACTACCCGTAGCAC-3'<br>(SEQ ID NO: 25) | |
| Probe 26 GAPDH | 5'-AATCCCATCACCATCTTCCA-3'<br>(SEQ ID NO: 26) | |

1-2. Preparation of Bead Array

A bead array was prepared by affixing beads (xMAP carboxylated microspheres available from Luminex Corporation, Austin, Tex.) to the respective primers.

1. Each of the probe prepared in Example 1-1 was dissolved in water as 100 μM concentration.
2. Beads were well homogeneously mixed and each 40 μl was pelleted to a freshly prepared tube.
3. 2 μl of the primer prepared and mixed with 20 μl of 0.1M MES buffer (pH 4.5) was mixed with the bead which is assigned depend on the probe type.
4. 1 μl of a freshly prepared 10 mg/ml 1-ethyl-3-(3-dimethylaminopropyl)-carbodiimide hydrochloride (EDC) solution (Pierce, Rockford, Ill.) solution was added to the mixture of microsphere and probe.
5. The resultant tube was violently agitated for about 30 min in the dark for activating reaction.
6. Following the activating reaction, 1 μl of a freshly prepared 10 mg/ml EDC solution was further added to the resultant tube, followed by further reacting for about 20 minutes.
7. Then, 500 μl of a 0.020% Tween-20 solution was added to each tube and well mixed.
8. The bead in each tube was centrifuged to remove a supernatant from the tube and 500 μl of a 0.1% sodium dodecyl sulfate (SDS) solution was further added to the tube, followed by agitating well.
9. The bead in each tube was centrifuged again to remove a supernatant from the tube.
10. The resultant bead was dissolved in 150 μl of a TE buffer (pH 8.0) and stored at 4° C. in the dark.

EXAMPLE 2

Assay of HPV Genotypes using Bead Array

2.1. Isolation of DNA from Samples

In order to isolate DNA from samples, uterine cervix cells sampled using a cotton swab were dissolved in 400 μl of a lysis solution and incubated in 10 μl of Proteinase K (20 mg/ml), followed by further reacting for about 15 minutes in boiling water.

2.2. PCR Amplification of HPV L1 Gene and a GAPDH Gene in DNA Sample

In order to detect and assay HPV genotypes, 5 μl of DNA prepared in Example 2-1 used as a template. The 1$^{st}$ PCR amplification of the HPV gene was performed with 0.4 uM of HPV primer set, 0.1 uM of GAPDH primer set, 0.1 mM of dNTP mix 75 mM of Tris HCl (pH 9.0), 20 ml of MgCl$_2$, 50 mM of KCl, 20 mM of (NH$_4$)$_2$SO$_4$, and 1.5 unit of Taq polymerase (Ultratools, Spain). The primers used herein have the following base sequences:

```
HPV primer sets
                                            (SEQ ID NO: 27)
YBT L1 F:      5'-gcmcagggwcayaayaatgg-3'

(SEQ ID NO: 28)
GP6-1:         5'-aataaactgtaaatcatattcctc-3'

GAPDH primer sets
                                            (SEQ ID NO: 29)
GAPDH F:       5'-gagtcaacggatttggtcgt-3'

(SEQ ID NO: 30)
GAPDH R:       5'-ttgattttggagggatctcg-3'
```

The reaction conditions of the PCR are as follows.

That is to say, A 5 minutes denaturation step at 95° C. was followed by 40 cycles of amplification with a PCR thermocycler (Master Cycler; Eppendorf, Hamburg Germany). Each cycle included a denaturation step at 95° C. for 30 seconds, an annealing step at 50° C. for 30 seconds, and an elongation step at 72° C. for 30 seconds. The final elongation step was prolonged for a further 7 minutes.

2-3. Labeling through 2$^{nd}$ Single Strand PCR

To identify the HPV type of the PCR product prepared in Example 2-2, in the present invention, amplification products were labeled through 2$^{nd}$ single strand PCR labeling. In order, to label the amplification product, 2 μl of a PCR product was used and single strand liner PCR amplification was performed with 0.5 uM of HPV reverse primer (SEQ ID NO: 28), 0.5 uM of GAPDH reverse primer (SEQ ID NO: 30), 50 uM of dATP, dGTP and dTTP mix, 20 uM of biotin-dCTP (Invitrogen), 75 mM of Tris HCl (pH 9.0), 20 mM of MgCl$_2$, 50 mM of KCl, 20 mM of (NH$_4$)$_2$SO$_4$, and 1 unit of Taq polymerase (Ultratools, Spain).

The reaction conditions of the PCR are as follows.

That is to say, A 5 minutes denaturation step at 95° C. was followed by 35 cycles of amplification with a PCR thermocycler (Master Cycler; Eppendorf, Hamburg Germany). Each cycle included a denaturation step at 94° C. for 30 seconds, an annealing step at 60° C. for 30 seconds, and an elongation step at 72° C. for 1 minute.

2-4. Hybridization using Bead Array

Each of the samples prepared in. Examples 2-1, 2-2 and 2-3 was dissolved in a 2× PnE hybridization buffer (YeBT, Co;) and hybridized using the bead array prepared in Example 1-2. After hybridization, reactions were allowed to take place for 5 minutes at 95° C. and 30 minutes at 40° C. After the reactions, each sample was transferred to a 96 well filter plate together with the bead, followed by washing 3 times using a TM hybridization buffer. After washing, the sample was agitated in 100 μl of a 500-fold diluted solution of fluorescent strepavidin-phycoerythrin conjugate(SAPE) (SigmaAldirich, S3402) for 15 minutes in the dark.

2-5. Signal Detection of Bead Array

The signal intensity of the hybridized amplicon for each well was measured by a Luminex 100 instrument. The Luminex 100 instrument using two lasers, one indicating a bead number, and the other indicating an amount of phycoerythrin reacted. While scanning 26 bead types in total, each HPV genotype can be determined as a mean fluorescence index (MFI).

EXAMPLE 3

Assay Results of HPV Genotypes using Patient Samples

Hybridization mixture which is prepared by mixing beads and hybridization solution was added to each labeled sample product. After the hybridization and washing step, hybridized samples and streptavidin-phycoerythrin reacted together. This fluorescence (phycoerythrin) signal amount was calculated at the bead array instrument.

As confirmed from the assay result, the patient sample was infected with HPV type 16. It was also confirmed that GAPDH amplification was carried out successfully, suggesting that there was no failure in the PCR. As shown in FIG. 1, an Any-probe for identifying HPV infection was also detected.

EXAMPLE 4

Assay Results of HPV Genotype with Multiple Infections

Figure 2:
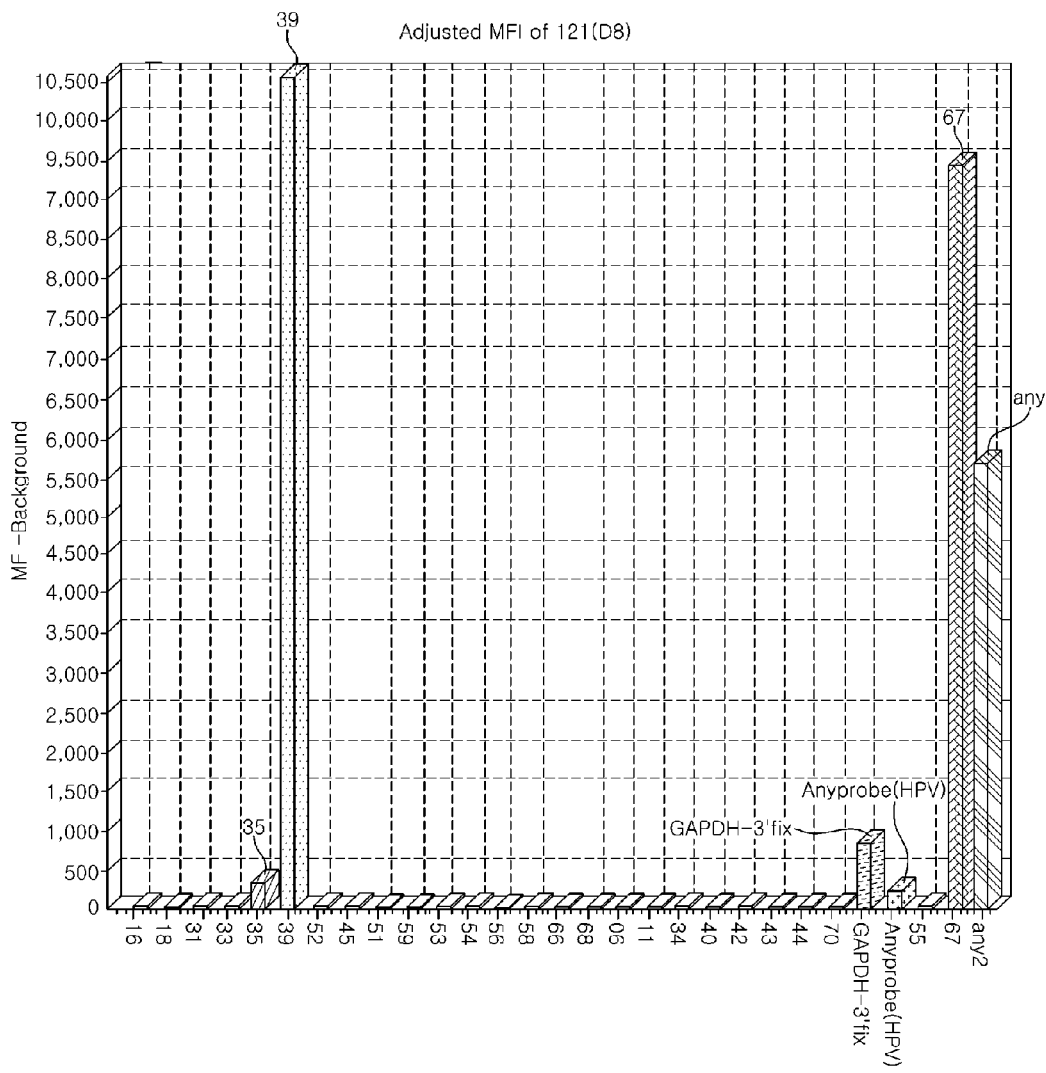
FIG. 2 is the analysis result from the sample has multiple infections with HPV type 35, 39 and 67 and a positive control signal of a GAPDH gene and a signal of any probe.

As the assay results shown in FIG. 2, it was confirmed that the patient sample was associated with multiple infections of HPV genotype types 35, 39 and 67.

INDUSTRIAL APPLICABILITY

As described above, detection probes and method according to the present invention can determine human papillomavirus (HPV) type with a high sensitivity and accuracy. In addition, the present invention enables detection of rare HPV infection(s) without specific probe but with the ANY probe in a simplified manner. Further, according to the present invention, it is possible to confirm whether negative results are accurate or not by GAPDH signal.

What is claimed is:

1. A set of probes for detecting a human papillomavirus (HPV) genotype, comprising: a nucleic acid of SEQ ID NO: 25, and one or more nucleic acids selected from SEQ ID NOs: 1-24.

2. A kit for detecting a human papillomavirus (HPV) genotype comprising the set of probes of claim 1.

3. The kit for detecting a human papillomavirus (HPV) genotype of claim 2, further comprising a set of primers for amplifying a human papillomavirus (HPV) L1 gene having nucleic acids of SEQ ID NOs: 27 and 28; a set of primers for specifically amplifying a GAPDH gene having nucleic acids of SEQ ID NOs: 29 and 30; and a GAPDH gene probe of SEQ ID NO: 26.

4. A method for detecting a human papillomavirus (HPV) genotype with a high sensitivity, the method comprising:
   (1) performing primary PCR amplification on an HPV L1 gene in a sample to be analyzed using a set of primers having nucleic acids of SEQ ID NOs: 27 and 28 specific to a region of L1 gene;
   (2) performing secondary PCR amplification on the primary PCR amplification product of the L1 gene using a primer of SEQ ID NO: 27 or 28, to yield a biotin-labeled, single-stranded L1 gene;
   (3) performing a hybridization reaction on the secondary PCR amplification product of the biotin-labeled, single stranded L1 gene with HPV genotype detection probes comprising a nucleic acid of SEQ ID NO: 25, and one or more nucleic acids selected from SEQ ID NOs: 1-24;
   (4) reacting the hybridization reaction product with fluorescent substance combined with streptavidin; and
   (5) measuring a fluorescent substance level to identify the HPV genotype.

5. The method of claim 4, wherein the secondary PCR amplification is performed using a primer of SEQ ID NO: 28.

6. The method of claim 4, wherein to yield the biotin-labeled, single-stranded L1 gene, the secondary PCR amplification is performed in the presence of a biotin-labeled dNTP.

7. The method of claim 4, wherein the probe is combined with a bead.

8. A method for detecting a human papillomavirus (HPV) genotype with a high sensitivity, the method comprising:
   (1) performing primary PCR amplification on an HPV L1 gene and a GAPDH gene in a sample to be analyzed using a set of primers having nucleic acids of SEQ ID NOs: 27 and 28 specific to the L1 gene and a set of primers having nucleic acids of SEQ ID NOs: 29 and 30 specific to the GAPDH gene;
   (2) performing secondary PCR amplification on the primary PCR amplification products of the L1 gene using a primer of SEQ ID NO: 27 or 28 and the primary PCR amplification products of the GAPDH gene using a primer of SEQ ID NO: 29 or 30, to yield a biotin-labeled, single-stranded L1 gene and GAPDH gene;
   (3) simultaneously performing hybridization reactions on both the secondary PCR amplification products of the biotin-labeled, single-stranded L1 and GAPDH genes with a HPV genotype detection probe comprising a nucleic acid of SEQ ID NO: 25, and one or more nucleic acids selected from SEQ ID NOs: 1-24 and a GAPDH specific probe of SEQ ID NO: 26, respectively;
   (4) reacting the hybridization reaction products with fluorescent substance combined with streptavidin; and
   (5) measuring fluorescent substance levels to identify the HPV genotype.

9. The method of claim 8, wherein the secondary PCR amplification is performed using a primer of SEQ ID NO: 28 on the primary PCR amplification products of the L1 gene and using a primer of SEQ ID NO: 30 on the primary PCR amplification products of the GAPDH gene.

10. The method of claim 8, wherein to yield the biotin-labeled, single-stranded L1 gene, the secondary PCR amplification is performed in the presence of a biotin-labeled dNTP.

11. The method of claim 8, wherein the probe is combined with a bead.

12. The method of claim 4 or 8, wherein the fluorescent substance is fluorescein, isothiocyanate, rhodamine, phycoerythrin, picocyanin, allophycocyanin, o-phthaldehyde, or fluorescarmine.

* * * * *